United States Patent [19]

Han et al.

[11] Patent Number: 5,468,487
[45] Date of Patent: Nov. 21, 1995

[54] EXTRACTED SUBSTANCE HAVING ANTI-HIV ACTIVITY

[75] Inventors: Young B. Han, 266-5 Jeongrung-dong, Seongbuk-ku; Jeong J. Mun; Hong K. Kyung; Jong B. Kim, all of Seoul; Kyung T. Kim, Kyungsangbuk-do; Hae R. Kim; Jeong H. Kim, both of Seoul; Hyun G. Shin, Kyungki-do; Kyung R. Kim, Seoul; Eun K. Hong, Kyungki-do; Choon W. Kim, Seoul, all of Rep. of Korea

[73] Assignees: Young Bok Han; Korean Association of Creation Research, both of Seoul, Rep. of Korea

[21] Appl. No.: 79,608

[22] Filed: Jun. 22, 1993

[30] Foreign Application Priority Data

Jun. 23, 1992 [KR] Rep. of Korea .................. 1992-10894

[51] Int. Cl.$^6$ .................................................... A61K 35/78
[52] U.S. Cl. ........................ 424/195.1; 514/934; 514/885
[58] Field of Search .......................... 424/195.1; 514/934

[56] References Cited

U.S. PATENT DOCUMENTS

| 4,795,739 | 1/1989 | Jon et al. ............................... 514/8 |
| 5,141,923 | 8/1992 | Byers et al. .......................... 514/12 |
| 5,178,865 | 1/1993 | Ho et al. ........................... 424/195.1 |

Primary Examiner—John W. Rollins
Attorney, Agent, or Firm—Birch, Stewart, Kolasch & Birch

[57] ABSTRACT

The present invention provides a extracted substance from a mixture of a non-fat starch from *Ricini Semen* and a root of *Coptis* sp. This substance is suitable for use in the therapeutic applications of AIDS.

4 Claims, 12 Drawing Sheets

EXTRACTED SUBSTANCE HAVING ANTI-HIV ACTIVITY

BACKGROUND OF THE INVENTION

1. Field of the Invention

The present invention relates to a novel extracted substance useful for antiviral inhibition against the human immunodeficiency virus (HIV) and a process for extracting the same. Specifically, the present invention relates to an extracted substance from a mixture of a non-fat starch from *Ricini Semen* and a root of Coptis sp. which exhibits a suitable anti-HIV activity without any side effects.

2. Description of the Prior Art

In 1983, it was found that HIV-1 is the causative agent of the acquired immunodeficiency syndrome (AIDS). Thereafter, several approaches to discover the genome of the virus and antiviral inhibitors thereof have been followed.

The selective infection of HIV on the helper T cell ($T_H$) induces a disorder of immune system and subsequently results in AIDS. Reverse transcribed viral genome of the virus usually remains in a chromosome of host cells in the latent period. At the end of the period, the vital proliferation induces a cell fusion to produce syncytia, and subsequently kill cells by an acute infection. Otherwise, the viral proliferation is continued without any significant cytopathic effects by a chronic infection.

When the membrane protein gp 120 of the virus recognizes CD4 receptors present in host cells, the virus then attaches thereto. The virus enters cells and subsequently changes its gene from RNA to DNA using a reverse transcriptase, and finally enters the chromosome of host cells.

The vital genome is replicated in the cells by several signals and factors required in a host cell proliferation, and then a long protein chain is produced by an action of a transacting regulatory proteins expressed by the virus gene. As a specific protease for HIV is then acted on the proteins essential for vital replication, some of these proteins is transformed into glyco proteins and subsequently assembled each other to form the whole virus.

Accordingly, in order to develop anti-HIV drugs, the following inhibitory functions against the viral replication cycle should be established through a chemical therapy.

(a) inhibition of an action between gp120 of the virus and CD4 receptors of host cells, (b) inhibition of an action of a reverse transcriptase to change RNA of the virus into proviral DNA, (c) inhibition of an action of viral regulatory proteins, (d) inhibition of cleavage of vital precursor proteins, (e) inhibition of an action of a glucosidase or a mannosidase for a prevention of modifications into glycoproteins, and so forth.

A number of drugs having selective anti-viral efficacy have hitherto developed using differences between HIV and human host cells. Such drugs, especially inhibiting the viral cell proliferation include dextran sulfates and peptide T having an inhibitory function of (a) described above; dideoxycytidines, dideoxyinosines and phosphonoformates having a function of (b). Beside these, the examples are ribavirin, castanospermine, GLQ 223, antisense oligonucleotides, protease inhibitor, and so forth. However, these drugs are still not being commercially available for AIDS.

In addition, zidovudine (azidothymidine, AZT) is concurrently used as a medicine for AIDS, but has serious disadvantages in that this usually induces side effects including symptoms such as headaches, emesis, high fevers and spots, injuries of hematogenous systems, nervous systems, and suppression of the liver function, and that a resistance to the drugs is often found in a long-term therapy.

We, inventors of the present invention, have intensively conducted a wide range of experiments in order to develop a potent inhibitors having high treatment effects. As a result, we have discovered that a novel extracted substance isolated from *Ricini Semen* and a root of Coptis sp. has significantly improved activity, and could accomplish the present invention.

SUMMARY OF THE INVENTION

It is therefore an object of the invention to provide a novel extracted substance which is useful as a inhibitor against HIV proliferation.

It is another object of the invention to provide the novel extracted substance which does not cause any side effects.

It is still another object of the invention to provide a therapeutic composition for AIDS comprising, as an active ingredient, the novel extracted substance of the present invention, in admixture and in association with conventional ingredients, such as carriers, excipients, extenders, and so forth.

It is still further object of the invention to provide a method for treating AIDS by using the novel extracted substance of the present invention.

Any additional objects of the invention will become apparent through reading the remainder of the specification.

DETAILED DESCRIPTION OF THE INVENTION

According to the present invention, a novel extracted substance isolated from *Ricini Semen* and a root of Coptis sp. is provided.

The extracted substance according to the invention is suitable to inhibit a certain step during the viral replication cycle, and it exhibits higher inhibitory activity on the HIV proliferation compared to other conventional inhibitors. Moreover, the extracted substance of the present invention is superior to other conventional ones in terms of not causing any side effects in test animals.

The extracted substance of the present invention is derived from a mixture of a non-fat starch from *Ricini Semen* and a root of Coptis sp. The mixing ratio of *Ricini Semen* and Coptis sp. is preferably from 2:5 to 5:2. A toxic component such as protein ricin and alkaloid ricinine which may present in the mixture is decomposed by a process depicted in FIG. 1.

The *Ricini Semen* used in the invention comprises 30 to 50% of fats. It has also proteins such as globulin, nucleoalbumin, glycoprotein, ricin, lipase, etc., and a toxic alkaloid ricinine. It is originated from India and the tropical Africa, and widely distributed except the cold latitudes. Especially, it is largely cultivated in the northeastern districts and plenty in America and Java. It is mainly shrub in the tropics and the subtropics while an annual herb in the temperate latitudes. The representative example of the *Ricini Semen* is *Ricinus Communis L.*

The Coptis sp., the other plant used in the invention is a perennial herb which is naturally grown or cultivated in hillocks of many countries in Asia. Examples are Chinese origins such as *Coptis chinensis* FRANCH, *Coptis deltoidis* C. Y. CHENG et HSIAO, *Coptis quinquesecta* W. T. WANG, *Coptis Teetoide* C. Y. CHENG and *Coptis chinensis* FRANCH var *brevisepala* W. T. WANG et HSIAO, Indian and Nepalese origins such as *Coptis teeta* WALL, Japanese origins such as *Coptis japonica* MAKINO var *dissecta* NAKAI, *Coptis japonica* MAKINO var *japonica* SATAKE, Korean origins such as *Jeffersomia dubia* BENTHAN et HOOKER, and so forth. The yellow or yellowish-brown components of Coptis sp. roots consist of mainly Alkaloid berberines, and contain palmatines, rateorrhizins, captisins, magnoflorines, etc. These components are considered to have stimulating functions for bile and pancreatin secretion, prevention functions for arterioscleroses, and antiphlogistic function. Thus, the Coptis sp. is clinically used as an antiphlogistic stomach and sedative agent for hyperemia and inflammation.

The extracted substance of the invention is obtained by an mixing extraction of said *Ricinus Communis L* and Coptis sp. root. In case of a separate extraction, the extract has a severe side effect and a poor anti-HIV activity.

Figure 1:
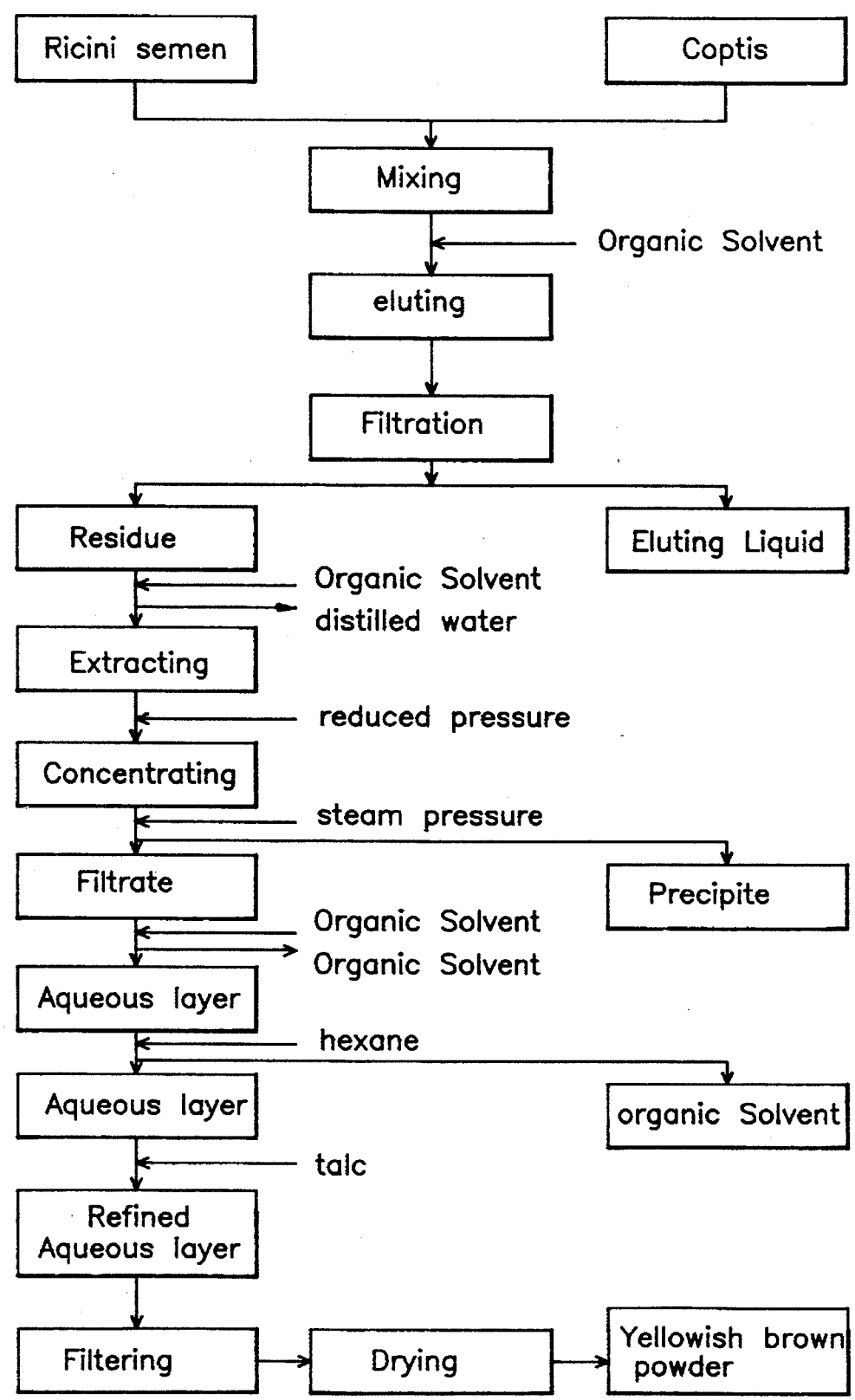
FIG. 1 is a diagram showing an extraction process for a product according to the invention.

Referring now to FIG. 1, a diagram showing an extraction process for a product according to the invention, the novel extracted substance of the invention can be prepared by a process which comprises the steps of:

(a) mixing a non-fat starch from *Ricinus Communis L* and a root of Coptis sp. in a weight ratio of 2:5 to 5:2, the most preferably 4:5 to 5:4;

(b) eluting the mixture with a organic solvent, preferably one or more fatty acid esters, the most preferably chloroform or hexane, at a room temperature of 20° to 25° C. for 20 to 25 hours;

(c) subjecting the resulting elute repeatedly to a filtration under a reduced pressure to carry out the separation of the residue;

(d) drying the residue to remove the organic solvent, and then adding about 5,000 mL of distilled water thereto;

(e) extracting the resultant under heating at 100° C. for 3 to 4 hours;

(f) concentrating the resulting extract under a reduced pressure to 1,500 mL, and then saturating the concentrate in vacuo to remove the precipitates;

(g) adding chloroform to the resulting extract, followed by agitating the mixture and separating the phase;

(h) removing the chloroform phase and then taking the aqueous phase by transferring oily substances into hexane with an addition of hexane to remove the organic solvent;

(i) refining the aqueous phase with a talc and subjecting the resultant to a filtration under a reduced pressure to give a filtrate; and (j) subjecting the resultant to a filtration through a membrane filter and then a lyophilization to give yellowish brown powders.

As the solvent, one or more solvents selected from the group consisting of aliphatic hydrocarbons, aromatic hydrocarbons, alcohols, $C_1$–$C_8$ halohydrocarbons comprising 1 to of the same or different halogen atoms, esters of fatty acid comprising methyl, ethyl, propyl, butyl or amyl, acetic acid esters, and ketones having $C_1$–$C_8$ aliphatic or aromatic groups may be used.

The extracted substance has not any toxic components such as protein ricin and alkaloid ricinine. The extracted substance according to the invention may be administered into the human body by means of various types of injection, for example, intravenous, intramuscular, subcutaneous and intraperitoneal injections dissolved in a distilled water or a physiological saline.

In further aspect, the present invention provides a composition for use in treating AIDS, which comprises, as an active ingredient, the novel extracted substance of the invention, in mixture or in association with conventional ingredients such as carriers, excipients, and other additives.

In still another aspect, the present invention provides a method for treating AIDS which comprises administering into the body the novel extracted substance of the present invention.

DESCRIPTION OF THE PREFERRED EMBODIMENTS

The present invention will be illustrated in greater detail by way of the following examples. The examples are presented for illustration purpose only and should not be construed as limiting the invention which is properly delineated in the claims.

EXAMPLE 1 In Vitro Assay

To evaluate toxicity of the extracted substances on T cell line (Sup $T_1$.H9), maximum acceptable concentrations of antiviral agents were determined as follows: To 0.5 to 0.8× $10^6$ test cells, the solution containing the extracted substances of the invention in several concentration from 1.0 ppm to 100 ppm as shown in Table 1 was added and incubated. After incubation, the number of cells was counted using a hemocytometer with trypan blue exclusion method to determine a reasonable concentration.

The recombination virus was used as a control in this example. The virus is pSVCAT in which HIV-1 nef unnecessary for a self-replication is substituted by chloramphenicol acetyltransferase (CAT). This virus has many advantages in that a syncytium-forming assay as well as a determination on the level of vital replication can be accomplished by evaluating CAT activity and that the problem of possible unsafety on nef gene can be solved since nef gene is expected to be necessary for in vivo viral replication as proved to be same in case of simian immune deficiency virus.

96-wells plates were added with $5\times10^4$ Sup $T_1$ cells and several concentrations of the extracted substances of the invention and then 50 $TCID_{50}$ pSVCAT was added thereto. After a three-day incubation the resulting multi-nucleate cells were counted. The observance thus measured was compared with that of AZT treated control as shown in Table 2 in view of the inhibition on the syncytium formation to determine an effective concentration.

H9 host cells were treated with the said virus and the substances of the invention in the effective concentration. In the interval of 3 days, ¾ of the media was replaced with a fresh media containing the same concentration of the substances of the invention. After a 9 day incubation, 1 mL of the culture was placed in a conical tube and then centrifuged at 350 g for 10 minutes to check the activities of reverse transcriptase and CAT.

Figure 2:
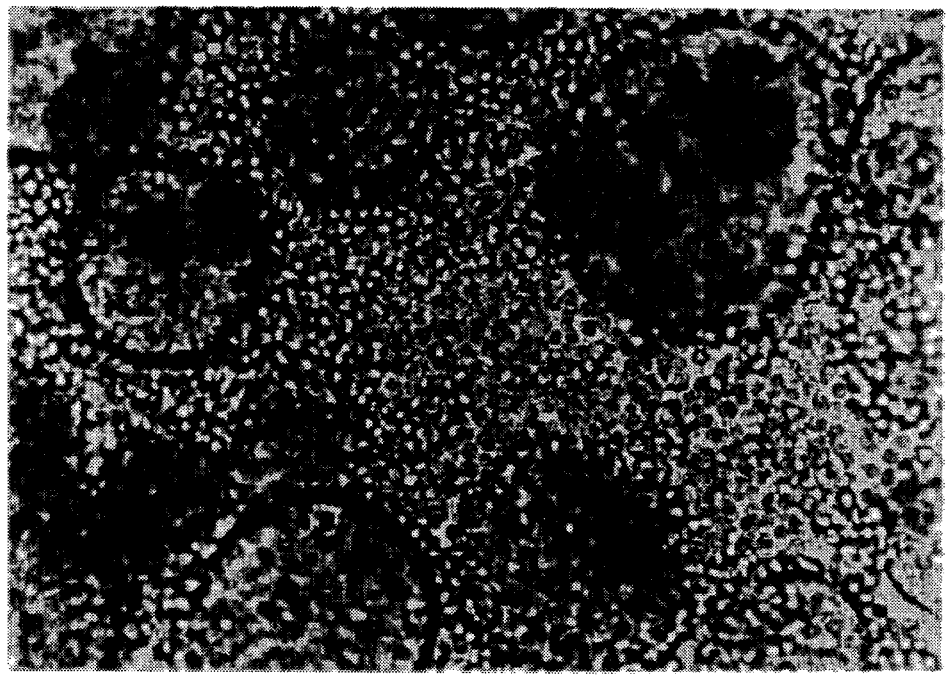
FIG. 2 represents a microphotograph of the test group for HIV infected cells as a control used in the invention.

The results are shown in Tables 1 to 3 and FIGS. 2 to 5. Table 2 represents effects of AZT and Table 3 those of berberine itself. FIG. 2 represents a microphotograph of the test group for HIV control used in the invention.

Figure 3:
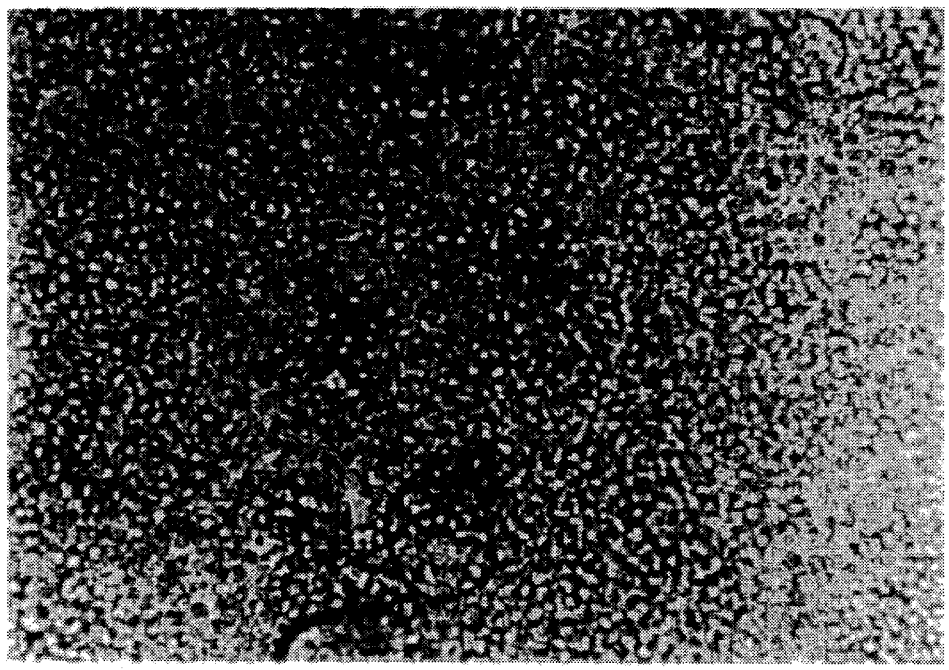
FIG. 3 represents a microphotograph of the test group administered in 10 µg/ml.
Figure 4:
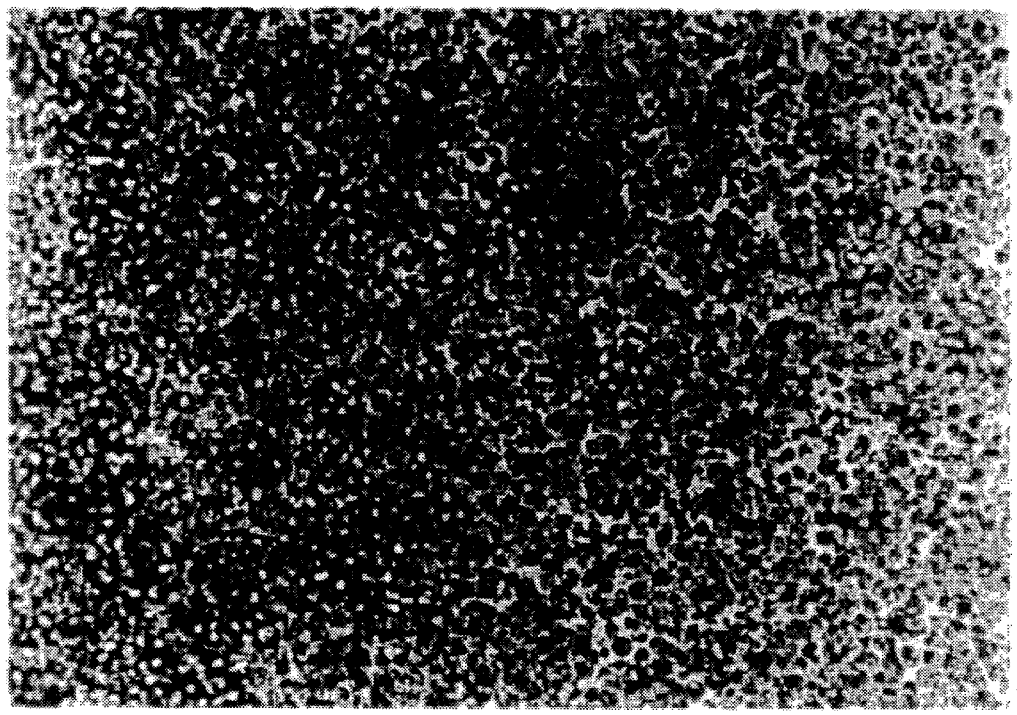
FIG. 4 represents a microphotograph of the test group administered in 50 µg/ml.
Figure 5:
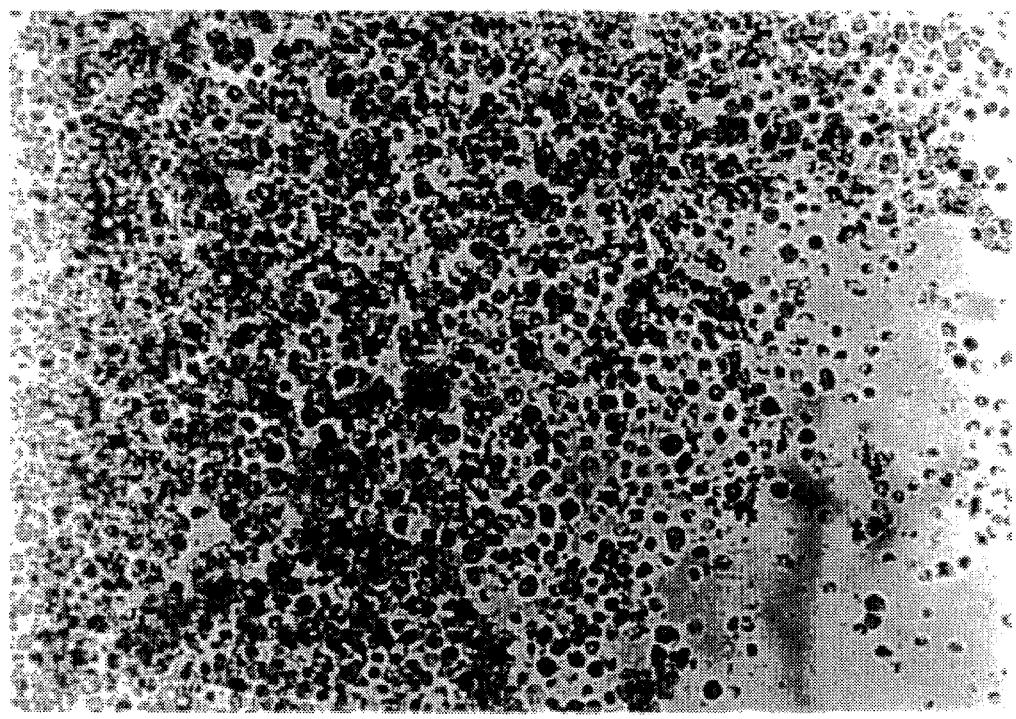
FIG. 5 represents a microphotograph of the test group administered in 100 µg/ml.

In Table 1 and FIGS. 3–5, it can be seen that the multiple-nucleate cells are not appeared at the concentration of 10 μg/mL or more (10 μg/mL, 50 μg/mL and 100 μg/mL). The substances of the invention is inferior to the AZT in view of the effect level at the same concentration, but the AZT induces serious side effects such as headaches, emesis and high fevers to the several parts of the human body in the long-term administration. From these, it is confirmed that the extracted substances of the invention have a strong antiviral activity on HIV proliferation without any side effects.

TABLE 1

| | The Substances of the Invention | | | | |
|---|---|---|---|---|---|
| Conc. (μg/mL) | 0 | 1.0 | 10 | 50 | 100 |
| No. of Multiple-Nucleate cells | 9 | 3 | 0 | 0 | 0 |
| Toxicity on the Host Cells | 0% | 0% | 20% | 30% | 40% |

TABLE 2

| | AZT | | | | |
|---|---|---|---|---|---|
| Conc. (μg/mL) | 0 | 0.05 | 0.2 | 1.0 | 5.0 |
| No. of Multiple-Nucleate cells | 8 | 1 | 0 | 0 | 0 |
| Toxicity on the Host Cells | 0% | 0% | 0% | 0% | 0% |

TABLE 3

| | Berberine | | | | |
|---|---|---|---|---|---|
| Conc. (μg/mL) | 0 | 0.1 | 0.5 | 1.0 | 3.0 |
| No. of Multiple-Nucleate cells | 9 | 8 | 5 | 2 | 1 |

TABLE 3-continued

| | Berberine | | | | |
|---|---|---|---|---|---|
| Conc. (μg/mL) | 0 | 0.1 | 0.5 | 1.0 | 3.0 |
| Toxicity on the Host Cells | 0% | 0% | 0% | 0% | 10% |

EXAMPLE 2

Figure 6:
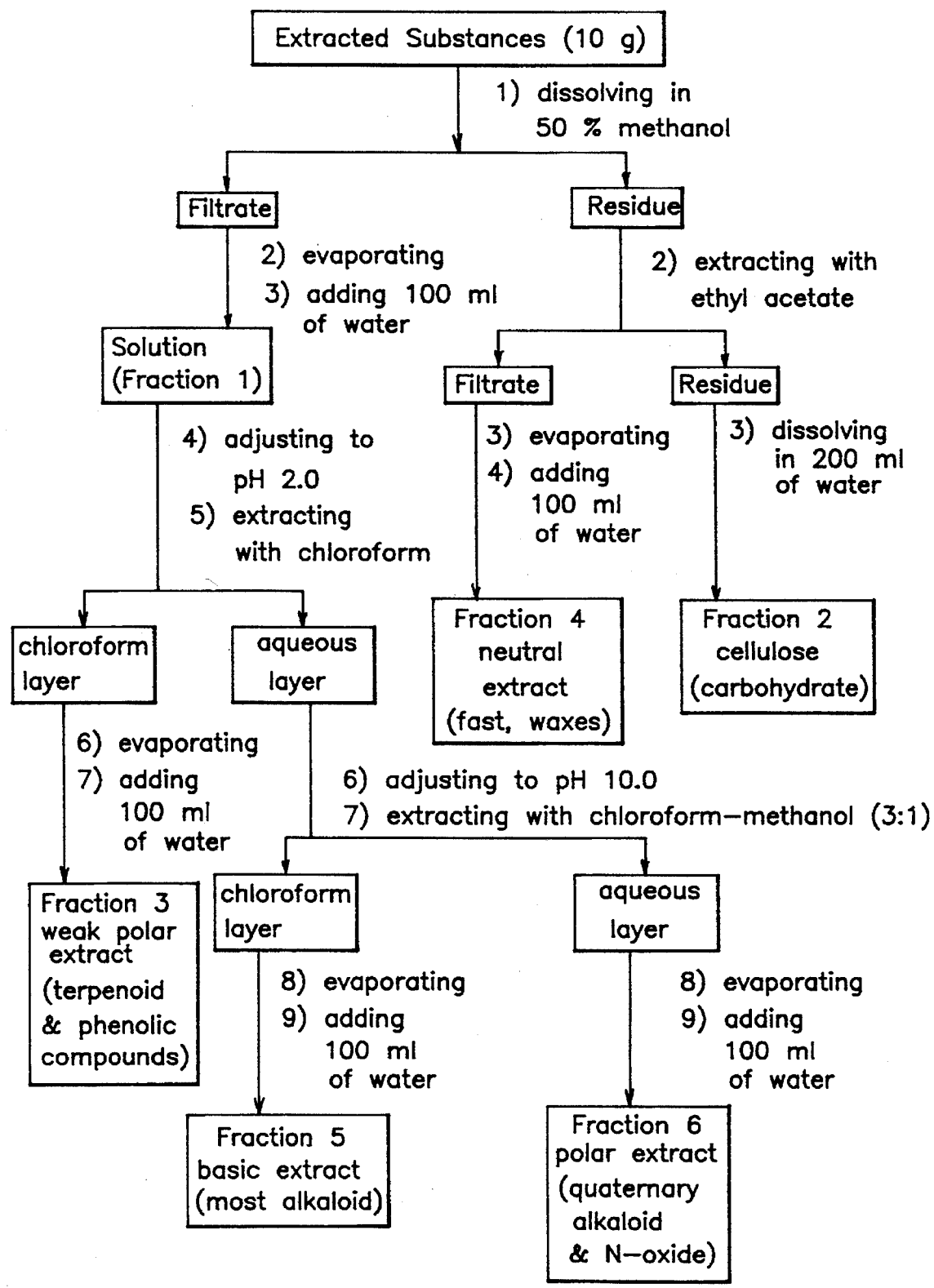
FIG. 6 is a diagram showing fractionating process for a product of the invention according to a polarity.

This example illustrates a separation of active ingredients from the extracted substances. The substances were separated into five different fractions in accordance with a method shown in FIG. 6 and then subjected to a thin layer chromatography (TLC). Each fraction was dissolved in a distilled water in the concentration 100 g of the extracted substance per 1 L of water except that the Fraction 2 (lower solubility in water) in 50 g/L. Independently, the same procedure was repeated with berberine (Siga Chem. Co., U.S.A.) which is a main quaternary alkaloid of Coptis sp. for comparison.

Ten g of the extracted substance was dissolved in 100 mL of a 1:1 mixed solvent of water and methanol and filtrated. The filtrate was evaporated to remove methanol and dissolved in 100 mL of a distilled water. The solution thus obtained was defined as a Fraction 1. The Fraction 1 was adjusted to pH 2.0 and then extracted with chloroform to separate into a chloroform layer and a aqueous layer. The chloroform layer was dried thoroughly and then dissolved in 100 mL of a distilled water. The solution thus obtained was defined as a Fraction 3. The aqueous layer was adjusted to pH 10.0 and then extracted with a mixed solution of chloroform and methanol (3:1) to separate into a chloroform layer and a methanol layer. The chloroform layer was dried and then dissolved in 100 mL of a distilled water to give a Fraction 5. The aqueous layer was evaporated to drying and then dissolved in 100 mL of a distilled water to give a Fraction 6.

In addition, the residual after the said filtration was extracted with ethyl acetate. The extract was evaporated to remove the solvent and dissolved in 100 mL of a distilled water to give a Fraction 4. The residue was dissolved in 100 mL of a distilled water to give a Fraction 2.

Each fraction was spotted on a normal phase thin layer chromatographic (TLC) sheet of silica gel in a conventional manner using a mixed solvent of butanol, acetic acid and water (4:1:1) as a developing solvent and a UV lamp for the detection of the sample. After spotting, the sample band was dried under a nitrogen stream. A filter paper was placed in TLC chamber, and the same solvent was poured into the chamber before running. Vacuum grease was used to seal the chamber covered with the cover glass.

Figure 7:
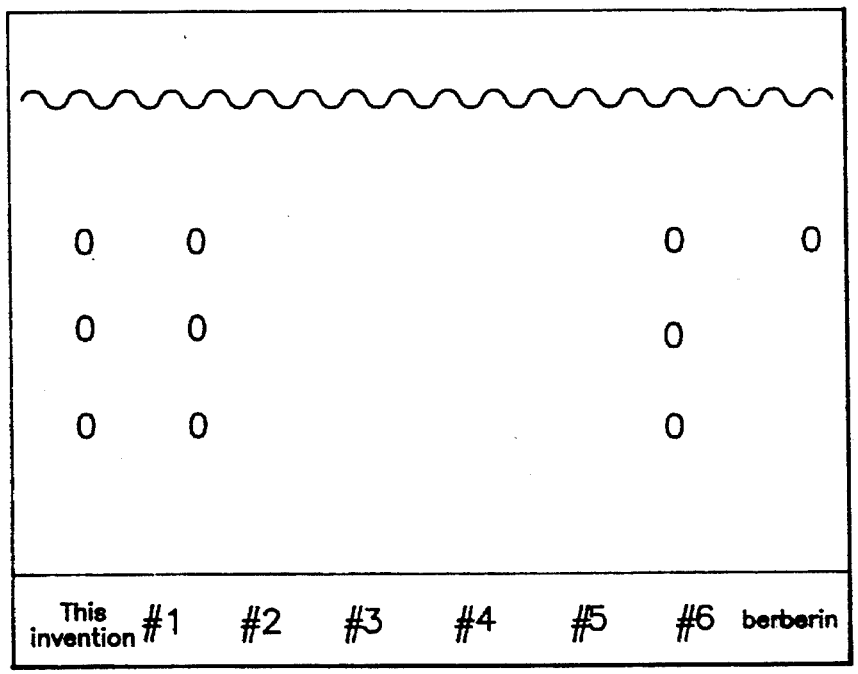
FIG. 7 represents a thin layer chromatograms for a fraction associated to FIG. 6 and berberine.

The results are shown in FIG. 7. Referring to FIG. 7, the Fractions 1 and 6 have the same TLC as the extracted substances of the invention. From This, it is confirmed that the extracted substances of the invention mainly consist of polar substances such as a quaternary alkaloid of the Fraction 6 and N-oxide, and have a $R_f$ value same as berberine.

EXAMPLE 3

This example illustrates a separation of active ingredients from the extracted substances by means of a ion exchange resin. The Fraction 6 of the Example 2 was separated into Fractions 6-S and 6-Q using Mono Q and Mono S ion exchange cartridges.

Figure 8:
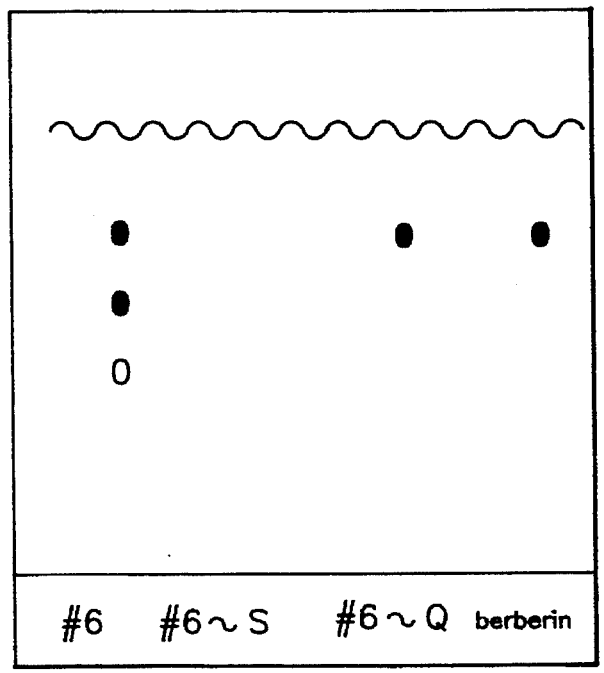
FIG. 8 represents a thin layer chromatograms for fractions of Fraction 6 fractionated by an ion exchange resin.

The Mono Q and Mono S cartridges were washed with methanol and saturated with a distilled water. 1.0 mL of Fraction 6 was loaded on each column and eluted using a mixed solvent of butanol, acetic acid and water (4:1:1). Each eluate was subjected to a thin layer chromatography (TLC). Independently, the same procedure was repeated with berberine for comparison. The results are shown in FIG. 8.

EXAMPLE 4

This example illustrates a purification of active ingredients from the extracted substances by means of a high performance liquid chromatography (HPLC). The Fraction 6 of the Example 2 was separated into Fractions 6-1, 6-2, 6-3, 6-4, 6-5 and 6-6 in accordance with a conventional method.

The organic solvent in each fraction was blown off and the residue was dissolved in 50 mL of a distilled water. To a Sep-Pak $C_{18}$ cartridge, 50 mL of the solution was loaded and washed with a sufficient water to remove a phosphate salt in the mobile phase. After disappearing a salty taste, the adsorbed substance was eluted using methanol.

Figure 9:
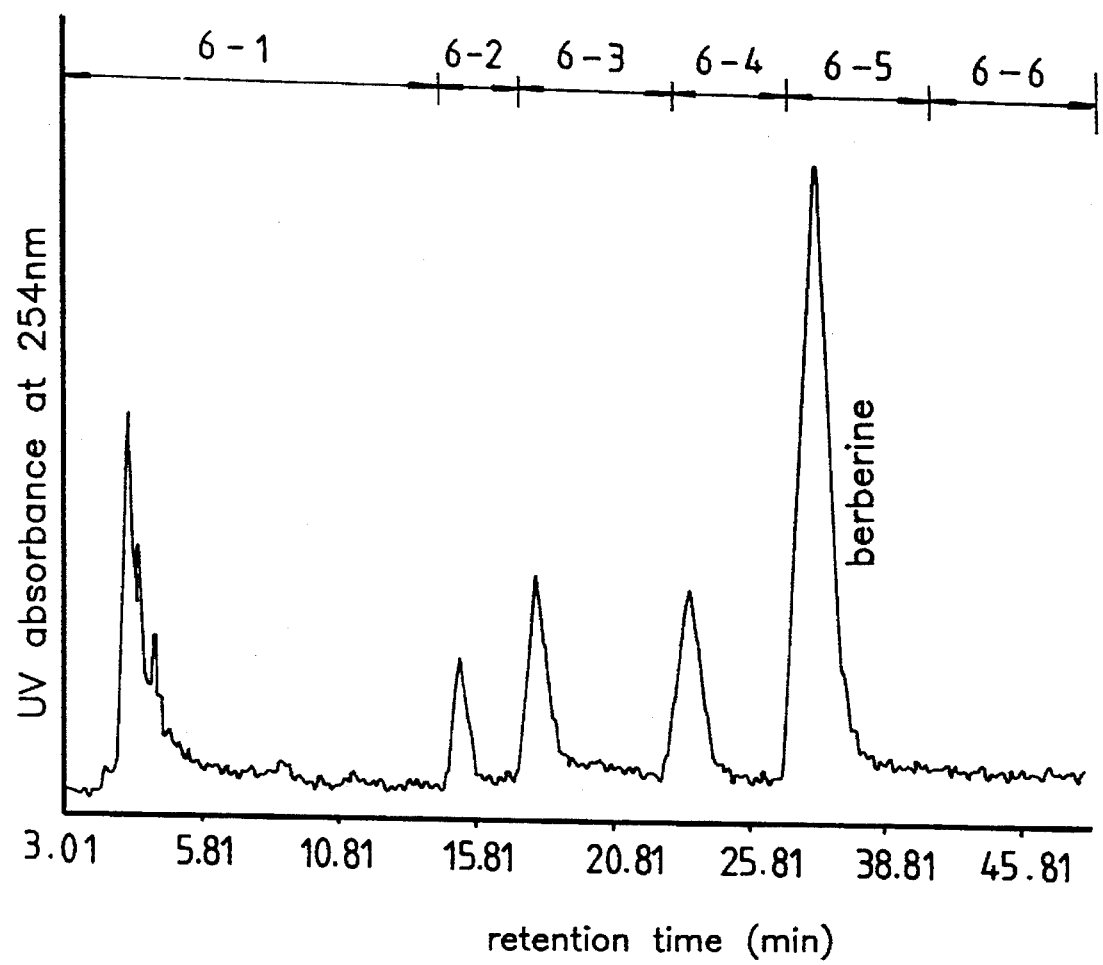
FIG. 9 represents high performance liquid chromatogram (HPLC) for Fraction 6.
Figure 10:
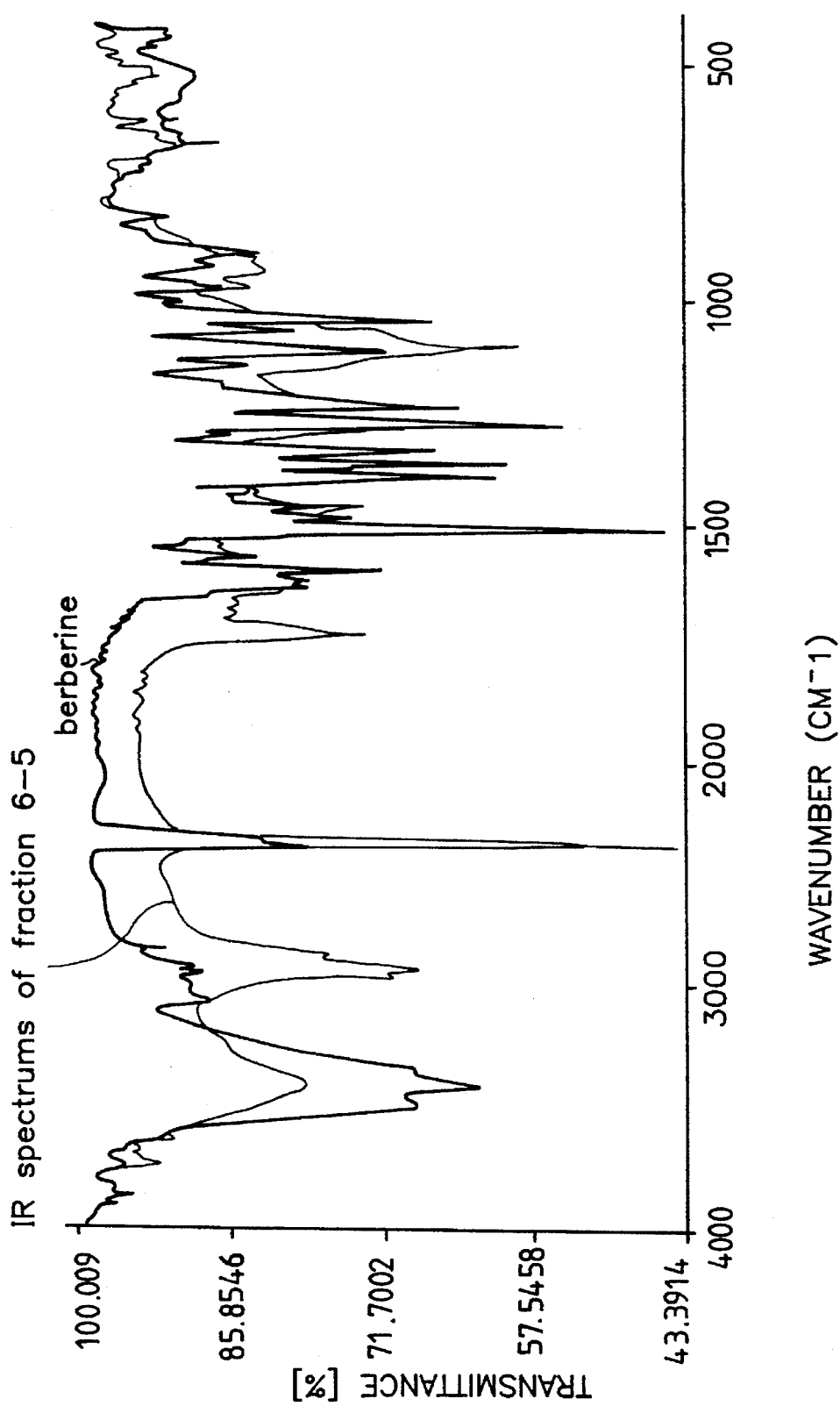
FIG. 10 represents IR spectra for Fraction 6-5 and berberine.

The resulting HPLC is shown in FIG. 9. Referring to FIG. 9, the Fraction 6-5 has the same retention time as berberine.

EXAMPLE 5

The Fraction 6-5 was analyzed to identify its chemical structure. To this end, infrared spectroscopy (IR), $^1$H-nuclear magnetic resonance spectroscopy ($^1$H-NMR), $^{13}$C-nuclear magnetic resonance spectroscopy ($^{13}$C-NMR) and mass spectrometry were employed. Independently, the same procedures were repeated with berberine for comparison. The results are shown in FIGS. 10 to 15.

Figure 11:
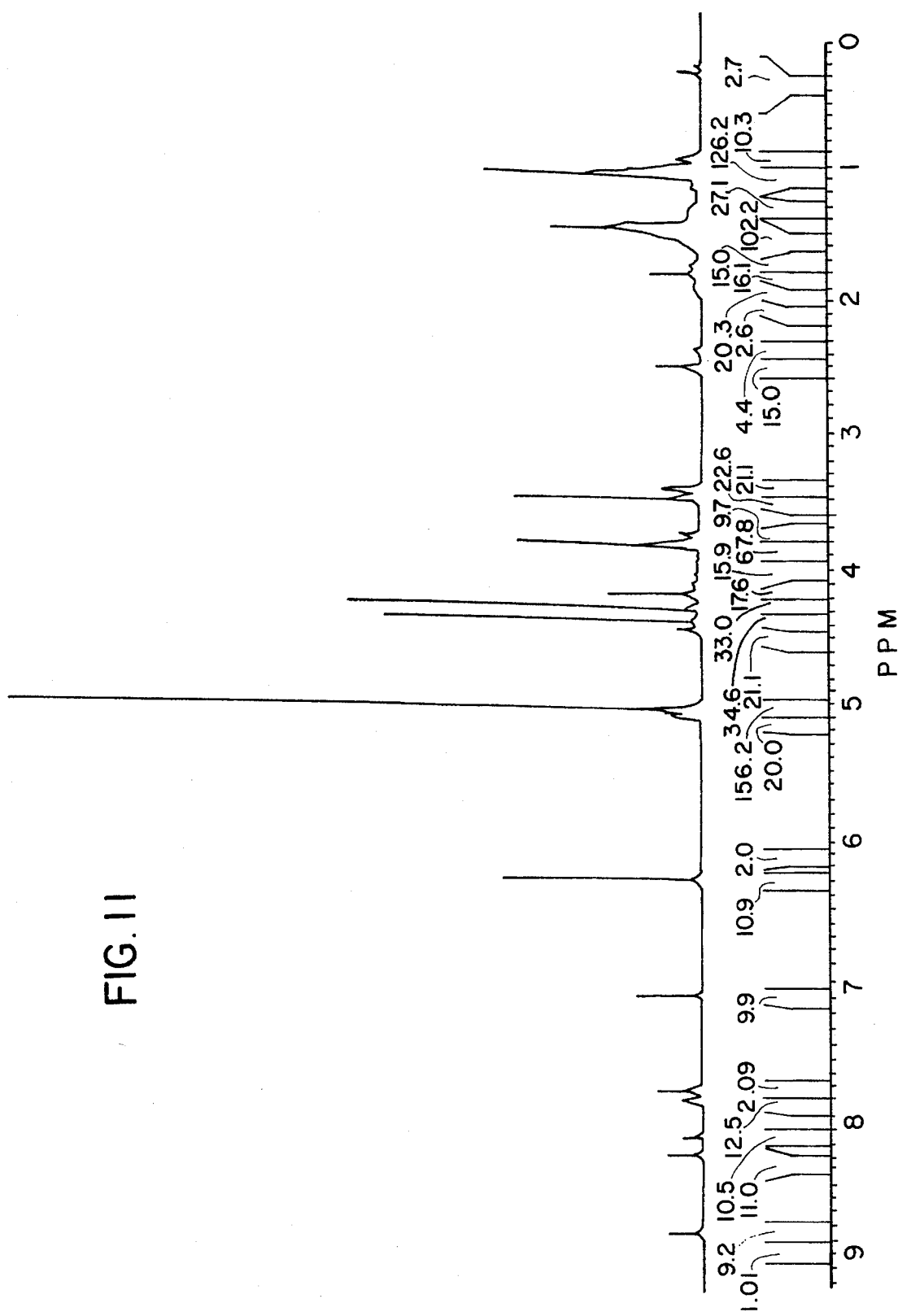
FIG. 11 represents a $^1$H-NMR spectrum for Fraction 6-5.
Figure 12:
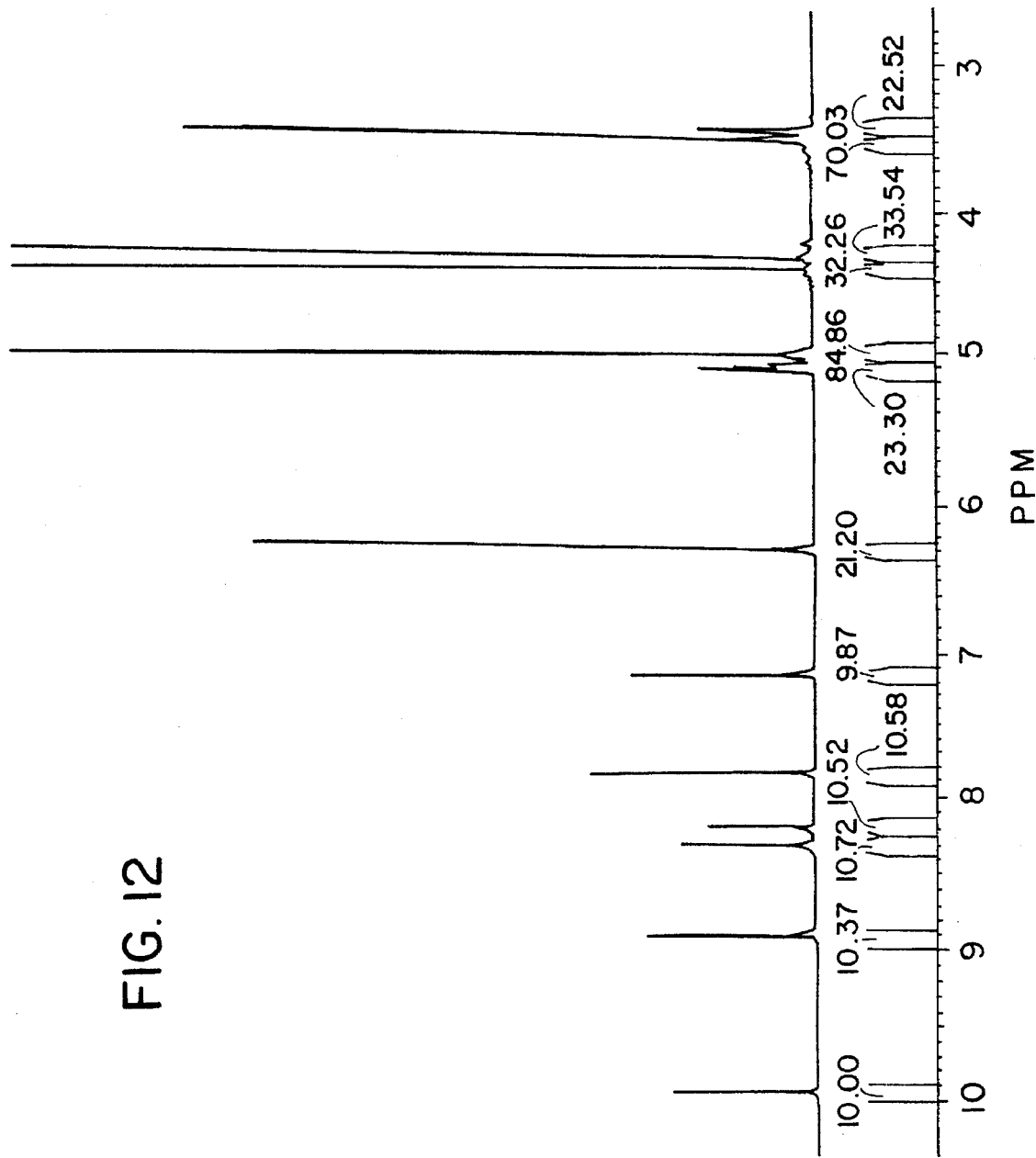
FIG. 12 represents a $^1$H-NMR spectrum for berberine.
Figure 13:
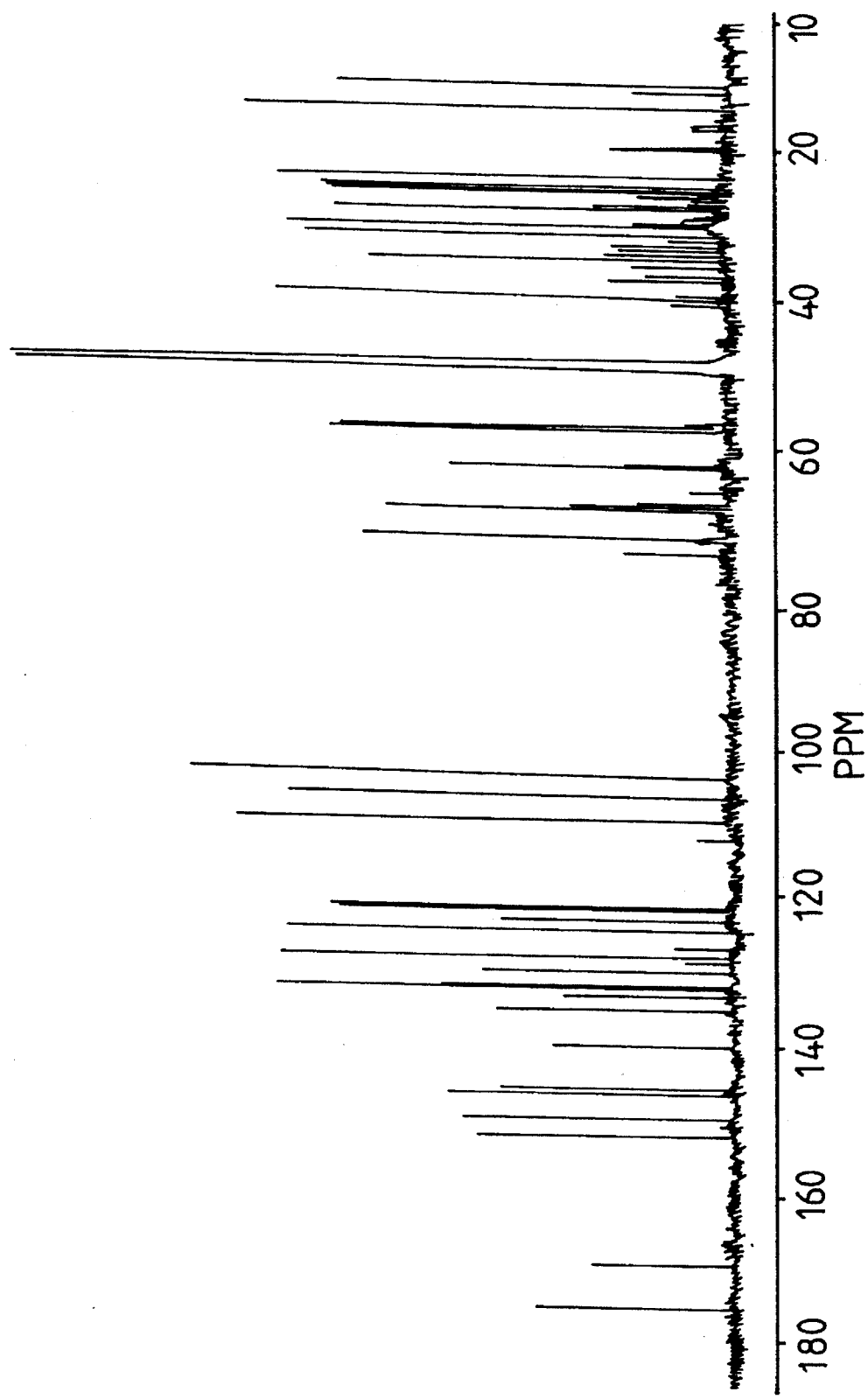
FIG. 13 represents a $^{13}$C-NMR spectrum for Fraction 6-5.
Figure 14:
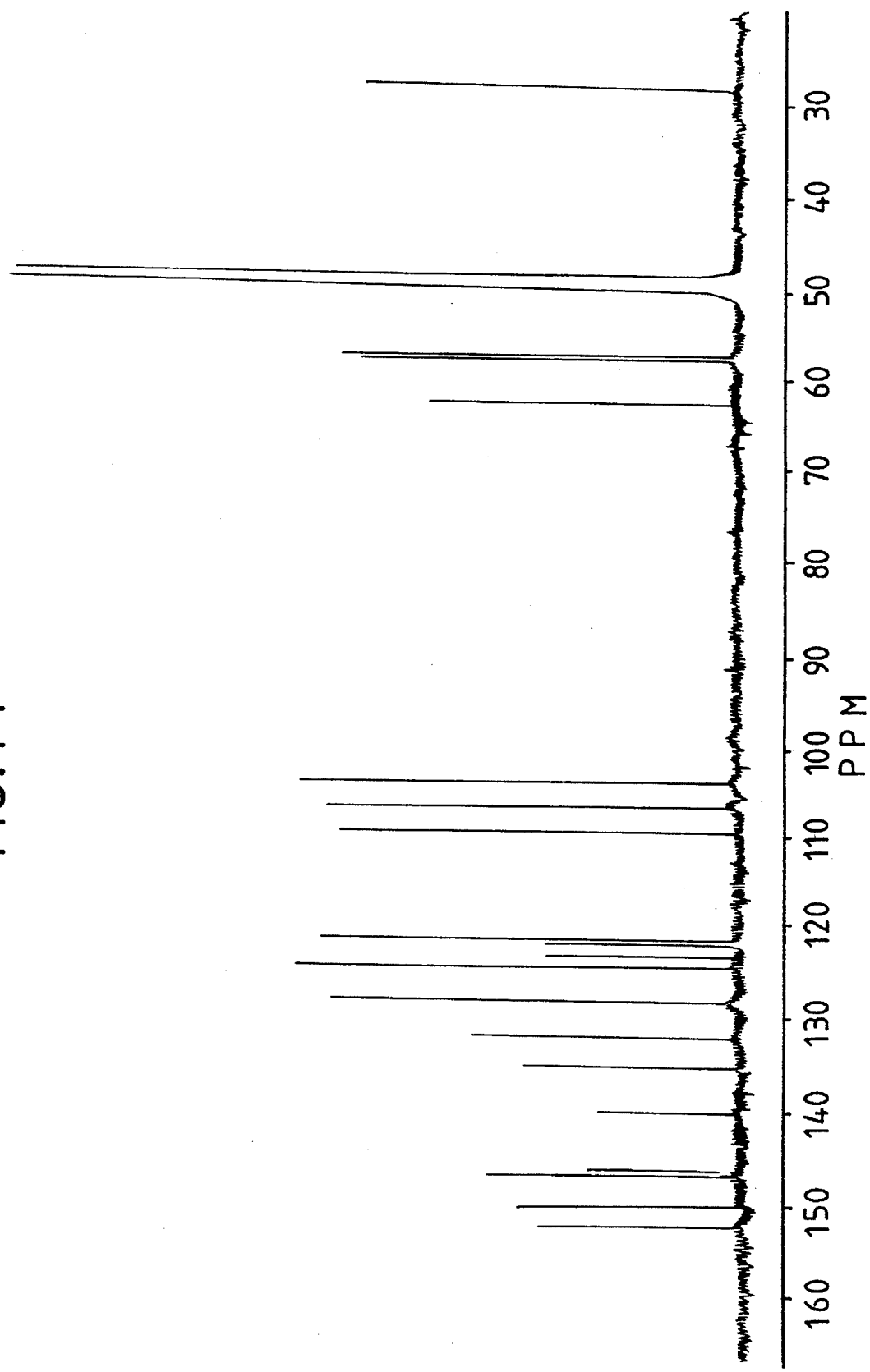
FIG. 14 represents a $^{13}$C-NMR spectrum for berberine.
Figure 15A:
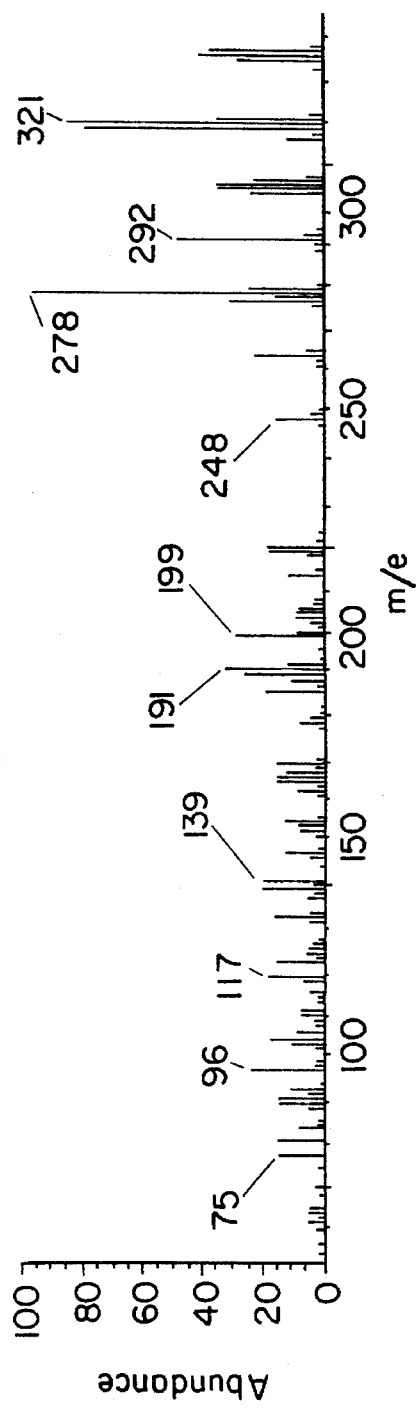
FIG. 15 represents MS spectra for Fraction 6-5 and berberine.
Figure 15B:
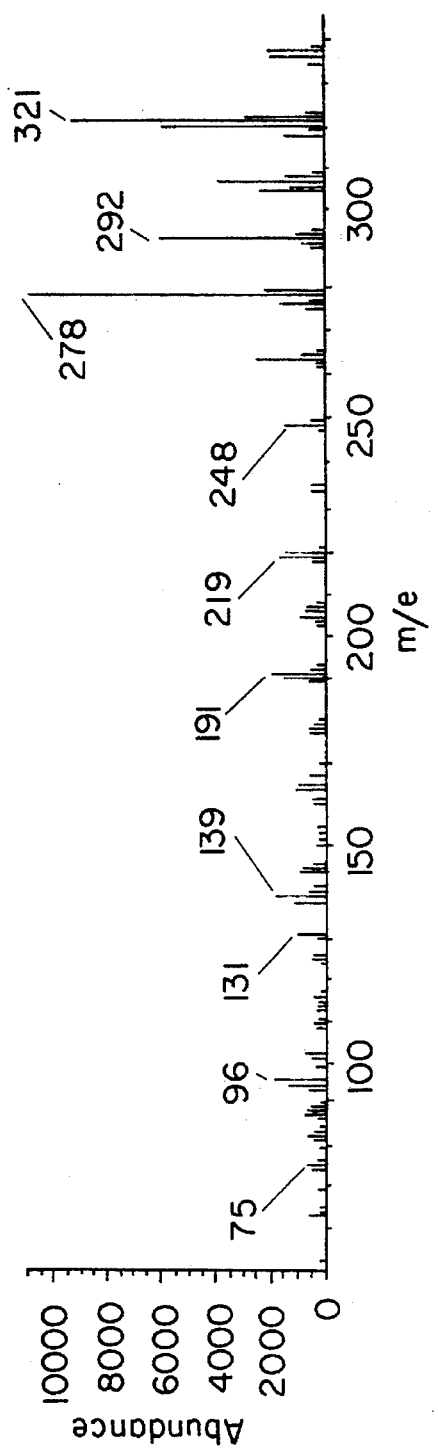

Referring now to FIGS. 10 to 15, FIG. 10 represents IR spectra for Fraction 6-5 (a) and berberine (b); FIG. 11 represents a $^1$H-NMR spectrum for Fraction 6-5; FIG. 12 represents a $^1$H-NMR spectrum for berberine; FIG. 13 represents a $^{13}$C-NMR spectrum for Fraction 6-5; FIG. 14 represents a $^{13}$C-NMR spectrum for berberine; and FIG. 15 represents MS spectra for Fraction 6-5 (a) and berberine (b).

From these results, it is concluded that the Fraction 6-5 comprises berberine even though it has a minor amount of impurities.

As discussed above, the extracted substance according to the invention is suitable to inhibit a certain step during the viral replication cycle, and it exhibits higher inhibitory activity on the HIV proliferation compared to other conventional inhibitors. Moreover, the extracted substance of the present invention is superior to other conventional ones in terms of not causing any side effects in test animals. Therefore, the extracted substance of the invention is expected to be suitable for use in the therapeutic applications of AIDS.

What is claimed is:

1. A process for preparing an extract having an activity of inhibiting HIV-induced syncytium formation in vitro which comprises the steps of:
   (a) mixing a non-fat starch from *Ricinus Communis L* and a root of Coptis sp. in a weight ratio from 2:5 to 5:2;
   (b) extracting the resulting mixture with an organic solvent at a temperature of 20° to 25° C. for 20 to 25 hours;
   (c) subjecting the resulting extract repeatedly to filtration under reduced pressure to obtain a filtrate and a residue;
   (d) drying the residue to remove remaining organic solvent, and then adding distilled water thereto;
   (e) heating the aqueous suspension obtained from step (d) at 100° C. for 3 to 4 hours to obtain an aqueous extract;
   (f) concentrating the aqueous extract under a reduced pressure, and then saturating the concentrate in vacuo to remove the precipitates;
   (g) adding chloroform to the aqueous extract, followed by agitating the mixture and separating the phases;
   (h) removing the chloroform phase and then further extracting the aqueous phase with hexane;
   (i) refining the aqueous phase with a talc and subjecting the refined aqueous phase to filtration under reduced pressure to obtain a filtrate;
   (j) further filtering the filtrate through a membrane filter and then lyophilizing the filtrate to give a yellowish brown powder.

2. The process according to claim 1 wherein the organic solvent one or more selected from the group consisting of aliphatic hydrocarbons, aromatic hydrocarbons, alcohols, $C_1$–$C_8$ halohydrocarbons comprising 1 to 6 of the same or different halogen atoms, esters of fatty acid comprising methyl, ethyl, propyl, butyl or amyl, acetic acid esters, and ketones having $C_1$–$C_8$ aliphatic or aromatic groups.

3. A method according to claim 1 wherein the weight ratio of non-fat starch from *Ricinus Communis L* and root of Coptis sp. is from 4:5 to 5:4.

4. An extract prepared by the method of claim 1.

* * * * *